US00PP37238P2

(12) United States Plant Patent
O'Connell

(10) Patent No.: US PP37,238 P2
(45) Date of Patent: Jan. 27, 2026

(54) ***SEDUM* PLANT NAMED 'LOVE'S FIRE'**

(50) Latin Name: *Sedum adolphi*
Varietal Denomination: LOVE'S FIRE

(71) Applicant: Altman Specialty Plants llc, Vista, CA (US)

(72) Inventor: Renee O'Connell, Pala, CA (US)

(73) Assignee: Altman Specialty Plants llc, Vista, CA (US)

( * ) Notice: Subject to any disclaimer, the term of this patent is extended or adjusted under 35 U.S.C. 154(b) by 0 days.

(21) Appl. No.: 19/264,410

(22) Filed: Jul. 9, 2025

(51) Int. Cl.
*A01H 5/02* (2018.01)
*A01H 6/32* (2018.01)

(52) U.S. Cl.
USPC ..... Plt./479
CPC ..... *A01H 6/328* (2018.05)

(58) Field of Classification Search
USPC ..... Plt./479
CPC ..... A01H 5/02
See application file for complete search history.

*Primary Examiner* — Kent L Bell

(57) ABSTRACT

A new and distinct cultivar of *Sedum adolphi* vermillion named 'Love's Fire' is disclosed, characterized by a more vivid vermillion color than any cultivar of *Sedum adolphi* known to the Inventor. Plants exhibit robust, moderately rapid growth, branching heavily at a young age. The new cultivar is a *Sedum*, typically produced as a container plant for the patio or as landscape plants, as well as a cultivar of ornamental purposes.

1 Drawing Sheet

Latin name of the genus and species: *Sedum adolphi.*
Cultivar denomination: 'LOVE'S FIRE'.

BACKGROUND OF THE INVENTION

The new cultivar, *Sedum adolphi* 'LOVE'S FIRE', is the product of chance discovery. The new cultivar originated as a naturally occurring whole plant mutation of the parent, *Sedum adolphi* 'Strawberry' (unpatented). The new cultivar 'LOVE'S FIRE' was discovered by the inventor, Renee O'Connell, in May 2022, in Vista, California, at a commercial greenhouse.

Asexual reproduction of the new cultivar 'LOVE'S FIRE' was first performed August 2022 in Vista, California, at a commercial greenhouse, by terminal vegetative cuttings. *Sedum adolphi* 'LOVE'S FIRE' has since produced multiple generations and has shown that the unique features of this cultivar are stable and reproduced true to type.

SUMMARY OF THE INVENTION

The cultivar 'LOVE'S FIRE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LOVE'S FIRE'. These characteristics in combination distinguish 'LOVE'S FIRE' as a new and distinct *Sedum* cultivar:

1. The new cultivar *Sedum adolphi* 'Love's Fire' displays a more vivid vermillion leaf color than any cultivar of *Sedum adolphi* known to the Inventor.
2. *Sedum adolphi* 'Love's Fire' vivid color enhances ornamental mixed plantings for holiday plantings, as well as patio plantings.

3. *Sedum adolphi* 'Love's Fire' produces robust, moderately rapid growth, branching heavily at a young age, the result is the enhancement of propagation in a commercial nursery environment.

PARENTAL COMPARISON

Plants of the new cultivar are similar to plants of the parent, in most horticultural characteristics, however, plants of the new cultivar differ in the following;

1. *Sedum adolphi* 'Love's Fire' forms branching clusters of strong vermillion leaves, whereas *Sedum adolphi* 'Strawberry' displays leaves of orange, blushed rose.
2. *Sedum adolphi* 'Love's Fire' displays a darker, more vivid color than does *Sedum adolphi* 'Strawberry'.
3. *Sedum adolphi* 'Love's Fire' grows faster than *Sedum adolphi* 'Strawberry'.

COMMERCIAL COMPARISONS

The new cultivar 'Love's Fire' can be compared to the unpatented commercial cultivar *Sedum adolphi* 'Firestorm'. Plants of the commercially grown *Sedum adolphi* are similar to plants of the new cultivar 'Love's Fire' in most horticultural characteristics. However, the new cultivar 'Love's Fire' differs in the following:

1. *Sedum adolphi* 'Love's Fire' displays leaves that are twice as wide as those of *Sedum adolphi* 'Firestorm'.
2. *Sedum adolphi* 'Love's Fire' forms more compact plants than does *Sedum adolphi* 'Firestorm', which forms taller, more sprawling plants.
3. *Sedum adolphi* 'Love's Fire' maintains its more controlled morphology, whereas *Sedum adolphi* 'Firestorm' tends to become an uncontrolled "weed" in time.

The new cultivar 'Love's Fire' can be compared to the unpatented commercial cultivar *Sedum* 'Gold Dust'. Plants of *Sedum* 'Gold Dust' are similar to plants of the new cultivar 'Love's Fire' in most horticultural characteristics. However, plants of the new cultivar 'Love's Fire' differ in the following:

1. *Sedum adolphi* 'Love's Fire' displays deep vermillion leaves, whereas *Sedum adolphi* 'Gold Dust' is a far lighter color, with gold accents.
2. *Sedum adolphi* 'Love's Fire' produces a larger branch rosette than does *Sedum adolphi* 'Gold Dust', which produces much smaller branch rosettes.
3. *Sedum adolphi* 'Love's Fire' produces a much larger cut than does *Sedum adolphi* 'Gold Dust', resulting in that a pot that can be filled with fewer cuts of *Sedum adolphi* 'Love's Fire' than of *Sedum adolphi* 'Gold Dust', enhancing production costs.

BRIEF DESCRIPTION OF THE PHOTOGRAPH

The photograph was taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new cultivar *Sedum* 'Love's Fire'.

The accompanying figure illustrates in full color a plant of *Sedum* 'Love's Fire', at about 6 months, grown at a nursery (approximately 2500 foot candles) in Vista, California in a 1-gallon pot.

DETAILED BOTANICAL DESCRIPTION

In the following description, color references are made to The Royal Horticultural Society Colour Chart, 2015 except where general terms of ordinary dictionary significance are used. The following observations and measurements describe 'Love's Fire' plants in a commercial greenhouse in Vista, California. Temperatures ranged from 1° C. to 29° C. night and day. No artificial light, photoperiodic treatments or chemical treatments were given to the plants. Natural light conditions were approximately 2500 fc of light. Measurements and numerical values represent averages of typical plant types.

Botanical classification: *Sedum adolphi* 'LOVE'S FIRE'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 1-gallon.

Growth habit: Semi-upright succulent. Starts upright, then trails.

Height: Approximately 10 to 12 cm.

Plant spread: Approximately 22 to 25 cm.

Branching characteristics: 2 to 6 basal occurring main branches. 2 to 3 sub-opposite lateral branches per main branch.

*Length*.—Main branches about 6 cm, lateral branches about 6 cm to 10 cm.

*Width*.—9 mm.

*Color*.—Near RHS Yellow-Green 145A.

*Texture*.—Glabrous.

*Appearance*.—Shiny.

*Strength*.—Moderately strong.

*Internode*.—About 1.2 cm.

FOLIAGE

*Arrangement*.—Sub-opposite, forming dense, evenly spaced rosettes.

*Foliar internode*.—About 4.5 mm.

*Average length*.—Mature foliage average range 3.2 cm to 4.4 cm.

*Average width*.—1.6 to 1.9 cm.

*Width at base*.—9 mm.

*Center (deepest) depth*.—8 mm.

*Shape of blade*.—Oblong.

*Apex*.—Acute to mucronate.

*Base*.—Truncate.

*Margin*.—Entire.

*Texture of top surface*.—Glabrous.

*Texture of bottom surface*.—Glabrous.

*Appearance of top surface*.—Moderately shiny.

*Appearance of top surface*.—Slightly shiny.

*Quantity*.—Average of 20 on one main branch/rosette.

*Color*.—Young foliage upper side: RHS Greyed-Orange 170A; flushed Orange-Red 34A. Apex Greyed-Orange 171A; flushed Orange-Red N34A. Base Yellow-Green 149D. Young foliage under side: RHS Greyed-Orange 170A; flushed Orange-Red 34A. Apex Greyed-Orange 171A; flushed Orange-Red N34A. Base and central streak Yellow-Green 149D. Mature foliage upper side: Center RHS Yellow-Green 144C. Margin Greyed-Orange 171B. Apex Greyed-Orange 172A; flushed Orange-Red N34A. Mature foliage under side: Center RHS Yellow-Green 144C. Margin Greyed-Orange 171B. Apex Greyed-Orange 172A; flushed Orange-Red N34A.

*Venation*.—Indistinguishable from leaf blade.

FLOWER

Not observed.

REPRODUCTIVE ORGANS

Not observed.

OTHER CHARACTERISTICS

Fruits and seeds: Not observed.

Temperature tolerance: Tolerates temperatures from approximately 0° C. to at least 32° C.

Disease/pest resistance: Neither resistance or susceptibility to normal diseases and pests of *Sedum* has been observed.

Drought tolerance: Tolerates at least 2 weeks of high temperatures without supplemental water, showing no serious damage to plant.

What is claimed is:

1. A new and distinct cultivar of *Sedum* plant named 'LOVE'S FIRE' as herein illustrated and described.

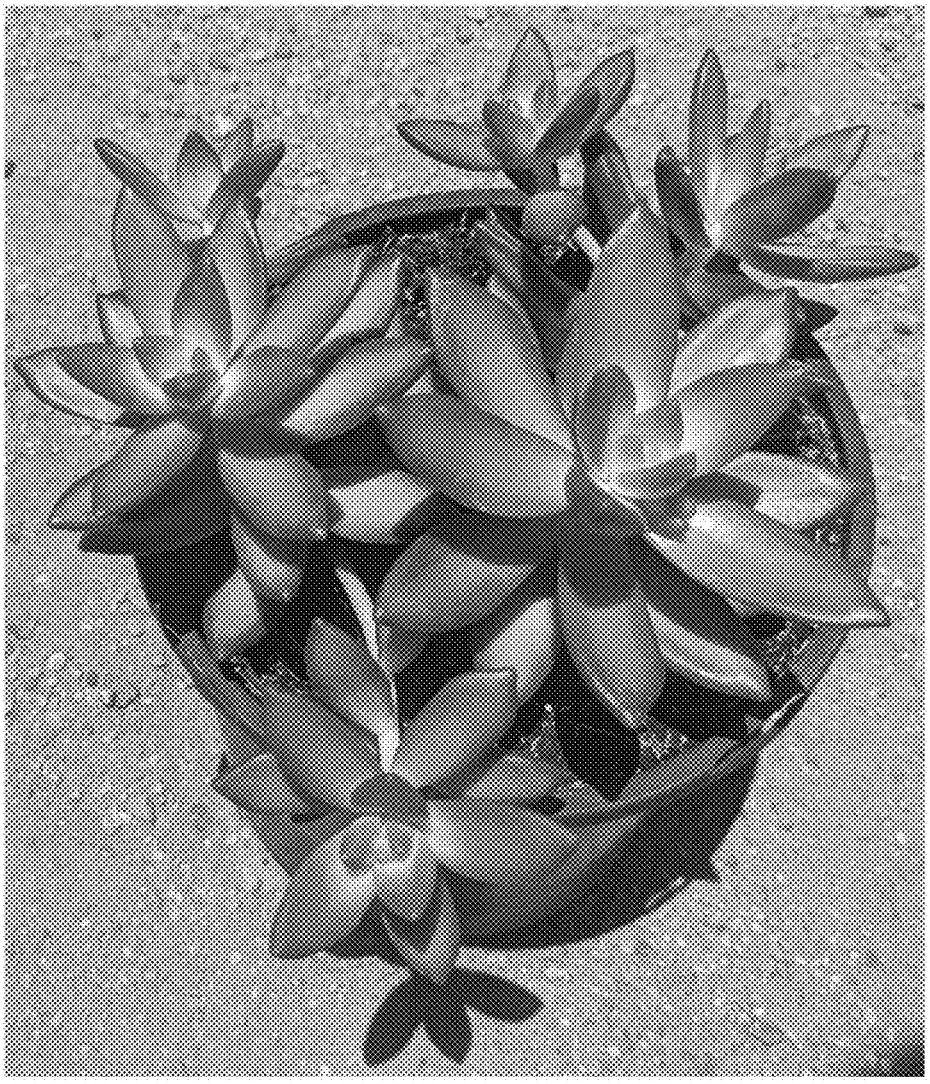

* * * * *